(12) United States Patent
Pedrozo et al.

(10) Patent No.: US 7,217,283 B2
(45) Date of Patent: May 15, 2007

(54) ORTHOPAEDIC IMPLANT FOR VASCULARIZATION OF THE FEMORAL HEAD

(75) Inventors: Hugo A. Pedrozo, Silver Lake, IN (US); Mark Heldreth, Mentone, IN (US)

(73) Assignee: Depuy Products, Inc., Warsaw, IN (US)

( * ) Notice: Subject to any disclaimer, the term of this patent is extended or adjusted under 35 U.S.C. 154(b) by 65 days.

(21) Appl. No.: 11/027,229

(22) Filed: Dec. 30, 2004

(65) Prior Publication Data

US 2006/0149362 A1 Jul. 6, 2006

(51) Int. Cl.
*A61F 2/06* (2006.01)
(52) U.S. Cl. .................. 623/1.13; 623/1.36; 623/23.64
(58) Field of Classification Search .................. 623/1.1, 623/1.13, 1.23, 1.36, 1.39, 1.41, 1.35, 23.61, 623/20.17, 23.64, 23.72, 23.76, 1.27, 16.11; 606/60, 76, 77, 86, 99, 194, 198
See application file for complete search history.

(56) References Cited

U.S. PATENT DOCUMENTS 5,102,413 A 4/1992 Poddar et al.
6,159,239 A * 12/2000 Greenhalgh ................ 623/1.13
6,679,890 B2 1/2004 Margulies et al.
6,929,659 B2 * 8/2005 Pinchuk ..................... 623/1.13
2003/0135214 A1 7/2003 Fetto et al.
2004/0153114 A1 8/2004 Reiley et al.

FOREIGN PATENT DOCUMENTS

FR 2070264 A 9/1971

OTHER PUBLICATIONS

European Search Report for European Application No. EP05257965.3-2318, May 10, 2006, 3 pgs.
Steve Copit, M.D. et al., "The Role of Elective Microvascular Surgery in Orthopedics", *Case Report #8*, http://www.orthopedictechreview.com/issues/feb00/case8.htm, printed on Mar. 3, 2004, 2 pgs.

* cited by examiner

*Primary Examiner*—William H Matthews

(57) ABSTRACT

An orthopaedic implant is provided for the treatment of avascular necrosis of the bone. The orthopaedic implant includes a hollow support structure and a synthetic vascular graft. The support structure defines a passageway and includes a proximal opening and a distal opening. The synthetic vascular graft is received, at least in part, within the passageway such that a proximal end portion of the synthetic vascular graft is received through the proximal opening of the support structure and a distal end portion of the synthetic vascular graft is received through the distal opening of the support structure.

17 Claims, 7 Drawing Sheets

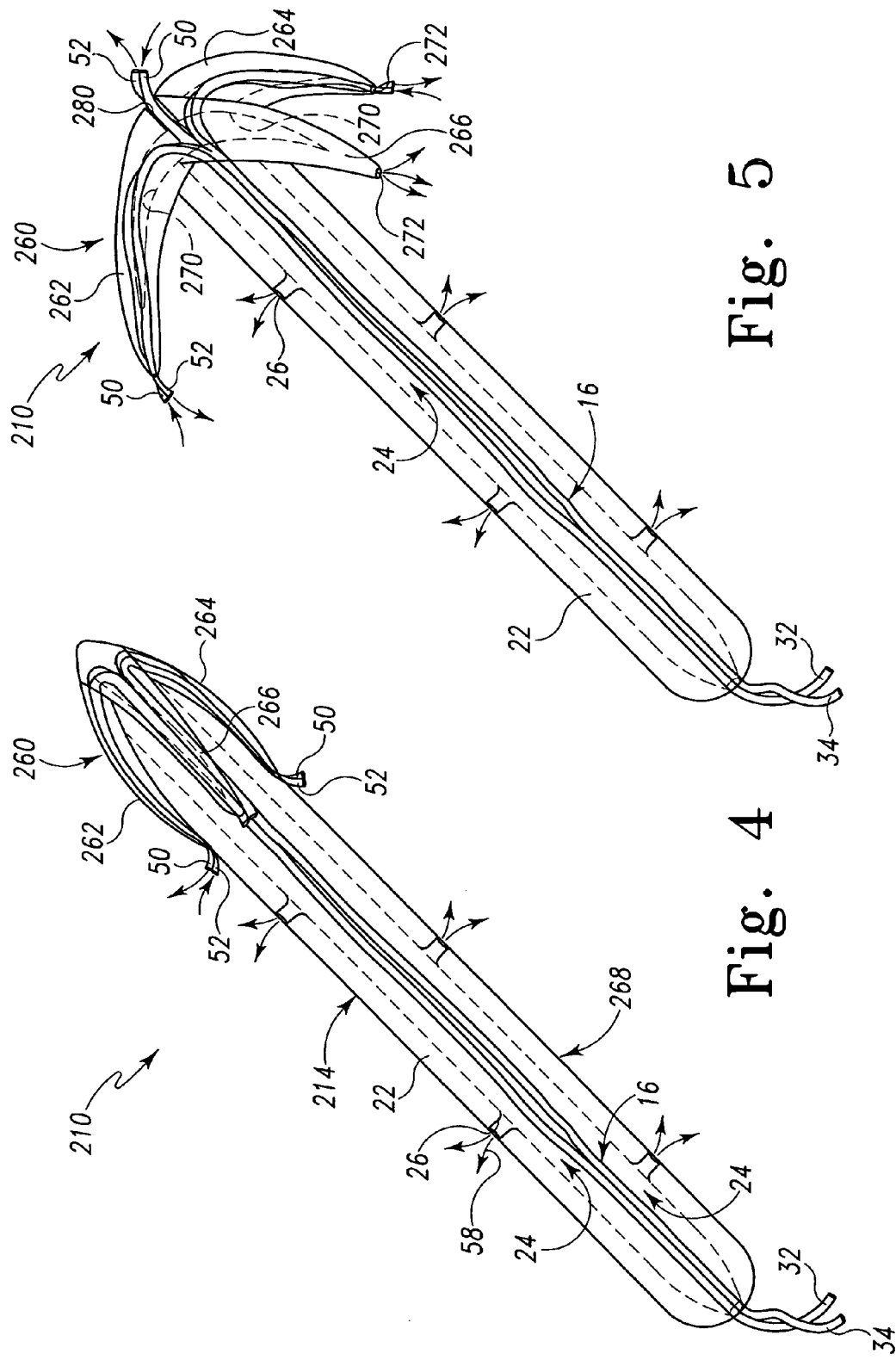

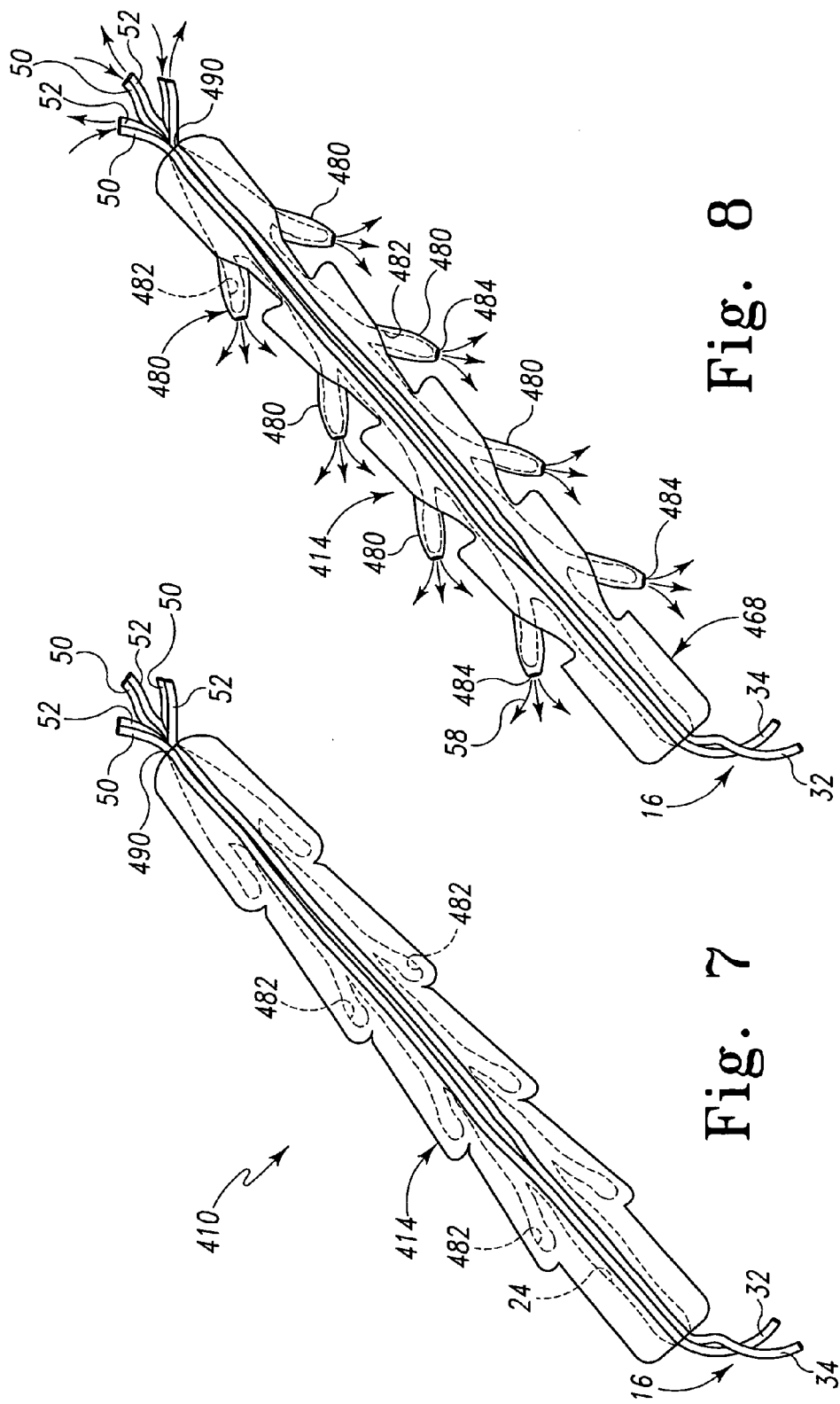

ORTHOPAEDIC IMPLANT FOR VASCULARIZATION OF THE FEMORAL HEAD

FIELD OF THE DISCLOSURE

The present disclosure relates generally to vascular grafts, and more particularly to synthetic vascular grafts used to treat avascular necrosis of a bone of a patient such as, for example, the femoral head. Specifically, the present disclosure relates to orthopaedic implants for vascularizing the bone of the patient.

BACKGROUND

Avascular necrosis (AVN), which is also known as osteonecrosis (ON), ischemic bone necrosis, or aseptic necrosis, is a debilitating disease resulting from the temporary or permanent loss of circulation to the bones resulting in localized bone death. The loss of proper blood flow can result from trauma or compromising conditions such as, for example, prolonged steroid use, alcohol use, gout diabetes, pancreatitis, venous occlusion, decompression disease, radiation therapy, chemotherapy, and Gaucher's disease.

AVN of the femoral head is a debilitating condition with oftentimes fast progression. Severe pain and limitation of movement can ensue in as short as two years with a 70–80% chance of complete collapse of the bone and surrounding articulating surface after three years if left untreated. For most patients, treatment becomes an ongoing process which inevitably results in arthroplasty. Various treatments for AVN which focus on salvaging the head of the femur or other bone or joint include core decompression, osteomy, bone grafting, and vascularized fibular grafting.

The latter is a surgical procedure in which an autologous fibular graft implant is used to support the head of the femur. The necrotic tissue is first removed and packed with autologous cancellous bone leaving room for the insertion of an autologous fibular graft with its vascular pedicle, the peroneal vessels, attached. To provide abundant blood flow to the head of femur, an anastomosis is performed between the lateral circumflex vessels and the fibula vascular pedicle. Although the procedure is oftentimes successful in stabilizing the femoral head and providing blood flow to the head, it carries the risk for donor sight morbidity, including, but not limited to, temporary loss of sensory function with the potential for compromised motor function in the distal part of the leg where the fibular graft was taken.

U.S. Pat. No. 6,679,890 discusses another method and device for treating AVN of the femoral head. The device disclosed in U.S. Pat. No. 6,679,890 augments the femoral head with bone cement. An open ended and fenestrated tube is inserted through a hole into the femoral neck and uncured bone cement is injected and cured at high pressure.

SUMMARY

The present invention comprises one or more of the features recited in the appended claims or the following features or combinations thereof:

An orthopaedic implant for the treatment of avascular necrosis of the bone includes a hollow support structure defining a passageway and a synthetic vascular graft received, at least in part, within the passageway. The hollow support structure includes a proximal opening and a distal opening such that a proximal end portion of the synthetic vascular graft is received through the proximal opening of the support structure and a distal end portion of the synthetic vascular graft is received through the distal opening of the hollow support structure.

The hollow support structure may be porous and/or may include a plurality of fenestrations between the proximal opening and the distal opening to provide communication between the passageway of the support structure and the surrounding environment. An outer surface and/or an inner surface of the support structure may be textured and may each have approximately a 60 nanometer surface roughness.

The support structure may include one or more of the following materials: a metal sponge, a resorbable polymer, a solid metal such as titanium, cobalt, chromium, steel, etc, a metal alloy, a polymeric sponge-like material, calcium phosphate, tricalcium phosphate, hydroxyapatite, ceramic, or a sintered ceramic material. The support structure may also include a resorbable or bioabsorbable material in addition to any other material(s) used.

The vascular graft of the orthopaedic implant includes a venous tube and an arterial tube. A distal end of the venous tube is trifurcated (i.e., split into three separate sections) and a distal end of the arterial tube is trifurcated. Each of the venous tube and the arterial tube have a diameter of approximately 3–6 mm and a length of approximately 15 cm. The vascular graft may include a protein-based polymer including one or more of the following materials: self-assembled collagen arteries, self-assembled basement membrane extracts, electro-spun collagen, elastin, and silk.

Illustratively, the hollow support structure includes a main body defining the passageway and one or more arms coupled to the main body and movable between a collapsed position adjacent to and engaged with the main body and an expanded position spaced-apart from the main body. Each arm includes a channel in fluid communication with the passageway of the main body. In one embodiment, the arms are positioned at a distal end of the main body while in another embodiment, the arms are positioned along a length of the main body.

The orthopaedic implant may also include a resorbable outer sheath surrounding the hollow support structure.

In other embodiments, an orthopaedic implant for the treatment of avascular necrosis of the bone includes a porous support structure defining multiple branched and interconnected passageways which terminate at an outer surface of the support structure. The channels may be coated with various substances such as, for example, extracellular matrix proteins or materials or collagen extracted therefrom, elasticfibronectin, etc. to promote among other things the attachment and differentiation of endothelial cells along the passageways. Illustratively, such an implant may be formed by mixing a calcium phosphate, fore example, with an organic polymer such that the organic polymer occupies the spaces where vasculature formation is desired. During processing, therefore, the organic polymer may be dissolved or burned off to leave behind the interconnected passageways.

A method of vascularizing a necrotic portion of a bone includes inserting a synthetic vascular graft into a passageway of a hollow support structure, implanting the hollow support structure and the synthetic vascular graft into a predrilled channel of the bone, and suturing the synthetic vascular graft to a vein and artery of the bone.

The above and other features of the present disclosure will become apparent from the following description and the attached drawings

BRIEF DESCRIPTION OF THE DRAWINGS

The detailed description particularly refers to the accompanying figures in which:

FIG. 4 is a perspective view of yet another orthopaedic implant of the present disclosure for the treatment of AVN showing the implant including a hollow support structure having a three-pronged head at a distal end of the implant in a retracted position and a synthetic vascular graft within the hollow support structure;

FIG. 5 is a perspective view of the implant of FIG. 4 showing the head in an expanded position;

FIG. 7 is a sectional view of yet another orthopaedic implant of the present disclosure for the treatment of AVN showing the implant including a hollow support structure having spring-loaded arms shown in a retracted position and a synthetic vascular graft within the support structure;

FIG. 8 is a sectional view of the implant of FIG. 7 showing the spring-loaded arms in an expanded position;

DETAILED DESCRIPTION OF THE DRAWINGS

Figure 1:
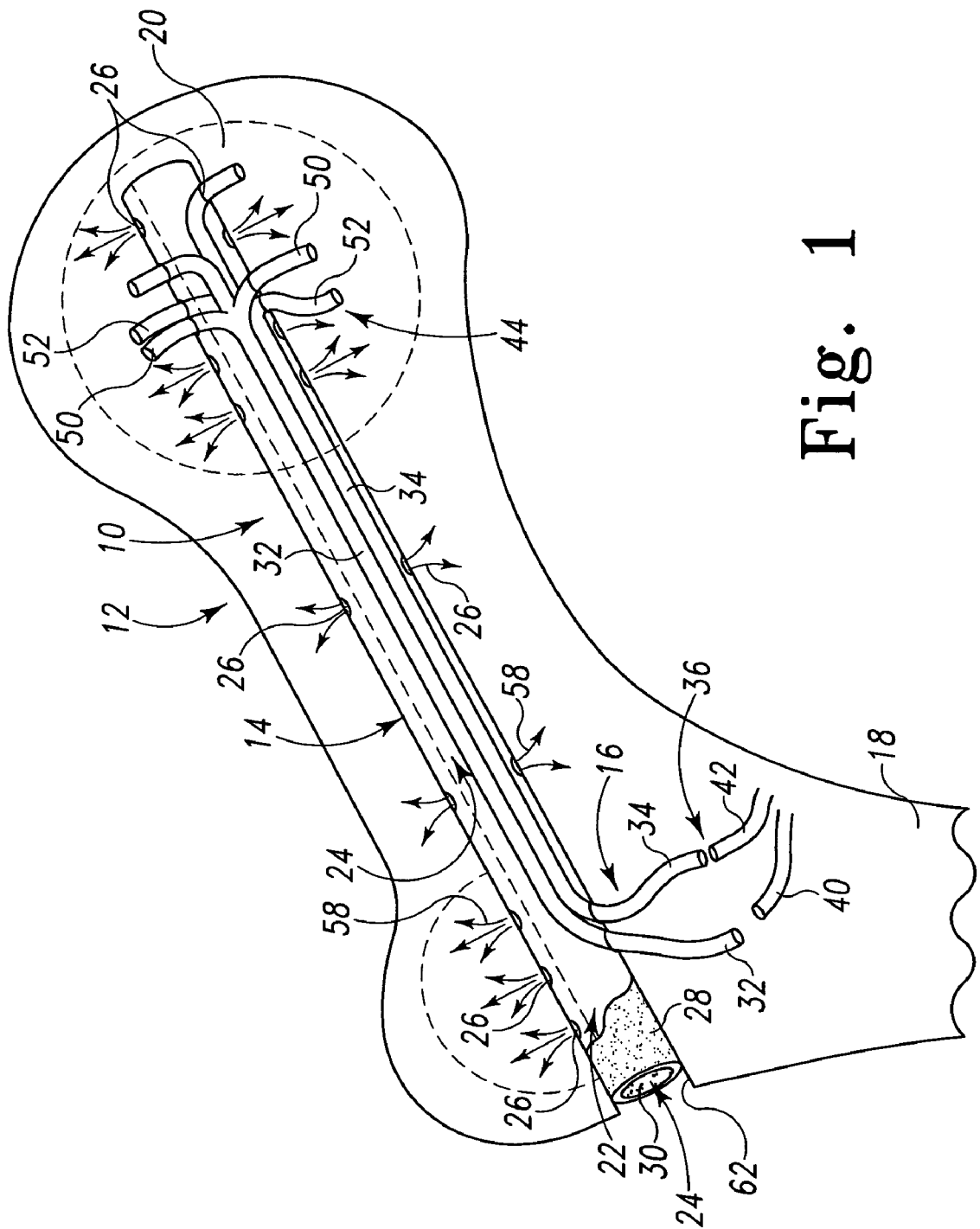
FIG. 1 is a sectional view of the head of a femur showing an orthopaedic implant of the present disclosure for the treatment of avascular necrosis (AVN) of the bone positioned within the head of the femur and including a hollow support structure or nail to provide support to the head of the femur and a synthetic vascular graft within the hollow support structure to communicate blood flow from a healthy part of the femur to the distal, damaged head of the femur.

An orthopaedic implant 10 for the treatment of avascular necrosis (AVN) of the bone and specifically of the femoral head 12 includes a support structure, illustratively a cannulated nail 14, and a synthetic vascular graft 16 within the support structure 14, as shown in FIG. 1. Providing a synthetic vascular graft 16 eliminates the need to harvest a portion of the patient's own fibula, including the peroneal vessels, to create an autologous graft. The cannulated nail 14 provides the femoral head 12 with structural or mechanical support independent of new bone growth while the synthetic vascular graft 16 provides a passageway for blood to flow from a healthy, proximal portion 18 of the femur to the necrotic, distal portion 20 of the femur to promote healing of the femoral head 12 by returning blood flow to that area.

As mentioned above, the cannulated nail 14 provides support to the femoral head 12. The cannulated nail 14 also provides protection for the synthetic vascular graft 16 which is threaded through the cannulated nail 14. Illustratively, the cannulated nail 14 includes an outer wall 22 defining a channel or passageway 24 along a length of the nail 14 between a first, open end and a second, open end. The passageway 24 serves as a channel for routing the synthetic vascular graft 16 up to the distal, necrotic portion 20 of the femoral head 12. The cannulated nail 14 is also porous or fenestrated, as shown by openings or apertures 26, to provide free fluid flow from the inner passageway 24 into the surrounding cancellous bone and vice versa. As is discussed in greater detail below, drugs or other bioactive agents may be delivered to the passageway 24 to slowly seep out through the openings 26.

Outer wall 22 may be made from various materials including, but not limited to, a solid metal such as titanium, cobalt, chromium, steel, etc, a metal alloy, a metallic sponge-like material, a resorbable polymer, a polymeric sponge-like material, calcium phosphate, ceramic, or a sintered ceramic material. Other materials suitable for implantation may be used as well. It is also understood that the outer wall 22 may include a bioabsorbable material in addition to the metal material used, for example. Further, the entire cannulated nail 14 providing the mechanical support structure for the femoral head 12 may be resorbable.

An outer surface 28 of the otuer wall 22 is nanotextured, as shown in FIG. 1. An inner surface 30, of wall 22 (defining inner passageway 24) may be nanotextured as well. This texturization of the outer and/or inner surface 28, 30 of wall 22 acts to promote cell attachment, proliferation, osteogenic differentiation, and/or overall fixation. Illustratively, the nanotextured surfaces 28, 30 may have a surface roughness of approximately 60 nm, for example. The cannulated nail 14, therefore, serves as a type of scaffold macro-support structure for the femoral head 12 as well as the vascular graft 16 while also providing a nano-support structure for cell invasion, attachment, proliferation, differentiation, etc.

The vascualar graft 16, as discussed above, is received through the passageway 24, or at least a portion of the passageway 24, of the cannulated nail 14. The vascular graft 16 is attached to existing veins and arteries of the femur to provide and promote blood flow to and from the necrotic portion 20 of the femoral head 12. As shown in FIG. 1, the synthetic vascular graft 16 includes two hollow tubes 32, 34 which illustratively represent a venous component and an arterial component. Each of the venous tube 32 and the arterial tube 34 is approximately 3–6 mm in diameter and approximately 15 cm in length.

The vascular graft 16 may be made of synthetic polymers or protein-based polymers. Commercially available vascular grafts such as the InterGard Knitted, Woven and Ultra Thin vascular grafts made by Intervascular® a Datascope Company (Montvale, N.J.) or the Vectra® Vascular Access Grafts, the Venaflo™ Vascular Grafts, the IMPRA Carboflo® and Distaflo® bypass grafts, and Bard® polyester grafts by Bard Peripheral Vascular (Murray Hill, N.J.) may also be used, for example. Other known commercially-available vascular grafts may be used as well. Vascular grafts made of protein-based polymers may include electrospun or extruded collagen, elastin, and/or an elastin/silk combination and extracellular matrix material such as small intestinal submucosa, for example, as well as components of extracellular matrix material such as collagen and/or self-assembled basement membranes, for example. Examples of extracellular matrix materials can be found in U.S. patent application Ser. No. 10/195,794 titled MENISCUS REGENERATION DEVICE AND METHOD, for example.

Each tube 32, 34 includes a proximal end 36 for attachment to an existing respective vein 40 and artery 42. A distal end 44 of each tube 32, 34 is trifurcated to provide three separate sections each being approximately 2–3 cm long. Although each tube 32, 34 is shown to be trifurcated (i.e., split into three separate sections) at the distal end 44, it is within the scope of this disclosure that the distal end of each tube may be bifurcated (i.e., split into two sections), split more than three sections, or not split into any sections at all. Illustratively, as shown in FIG. 1, each trifurcated section or branch 50 of venous tube 32 and each trifurcated branch 52 of arterial tube 34 exits the inner passageway 24 of the hollow nail 14 through different openings or apertures 26 formed through outer wall 22 of nail 14 to deliver blood flow to the necrotic portion 20 of the femoral head. Further illustratively, the branches 50, 52 are shown to exit at each of the caudal, medical, and rostral areas of the femur or femoral head 12. The branches 50, 52 may exit the passageway 24 at other areas or openings of the support structure 14 as well. Blood flow is therefore brought to the necrotic portion 20 of the femoral head 12 from artery 42 through arterial tube 34 and out the branches 52 to promote healing and regeneration of the necrotic portion 20 of the femoral head 12. It is contemplated that venous return of the blood flow can occur via the return vessel or tube 32 or simply through luminal passageway 24 of the cannulated nail 14.

The luminal or inner surface 30 of the wall 22 of the nail 14 and/or the entire passageway 24 of the nail 14 may be filled with a bioactive agent in a slow release carrier for various purposes such as the treatment of pain, infection, the stimulation of osteogenesis or angiogenesis, and others. The release of such a bioactive agent is illustrated by arrows 58. The bioactive agent may seep out through the porous or fenestrated outer wall 22 via pores and/or small openings or apertures 26, as shown in FIG. 1. The cannulated nail 14 may be pre-filled with such agents prior to insertion into the femoral head or a device (not shown) may be used to inject such agents into the passageway 24 of the nail 14 after the nail 14 has been implanted. The passageway 24 of nail 14 may, therefore, act as a reservoir for osteogenic or other such bioactive agents.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_β$superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

A method of vascularizing a necrotic portion of a bone, such as the femoral head 12, includes drilling a passageway or cavity 62 within the femoral head and inserting the implant 14 into the predrilled passageway 62 shown in FIG. 1, for example. The entire implant 10 (including the nail 14 and vascular graft 16), therefore, is inserted into the passageway 62. In the alternative, however, the cannulated nail 14 may first be inserted into the predrilled passageway 62 and the synthetic vascular graft 16 may then be threaded through the inner passageway 24 of the nail 114. In any event, once the nail 14 and synthetic graft 16 are properly positioned within the passageway 62 drilled in the femoral head 12, the proximal end 36 of the venous tube 32 and the arterial tube 34 are sutured to a respective healthy femoral vein 40 and artery 42.

Figure 3:
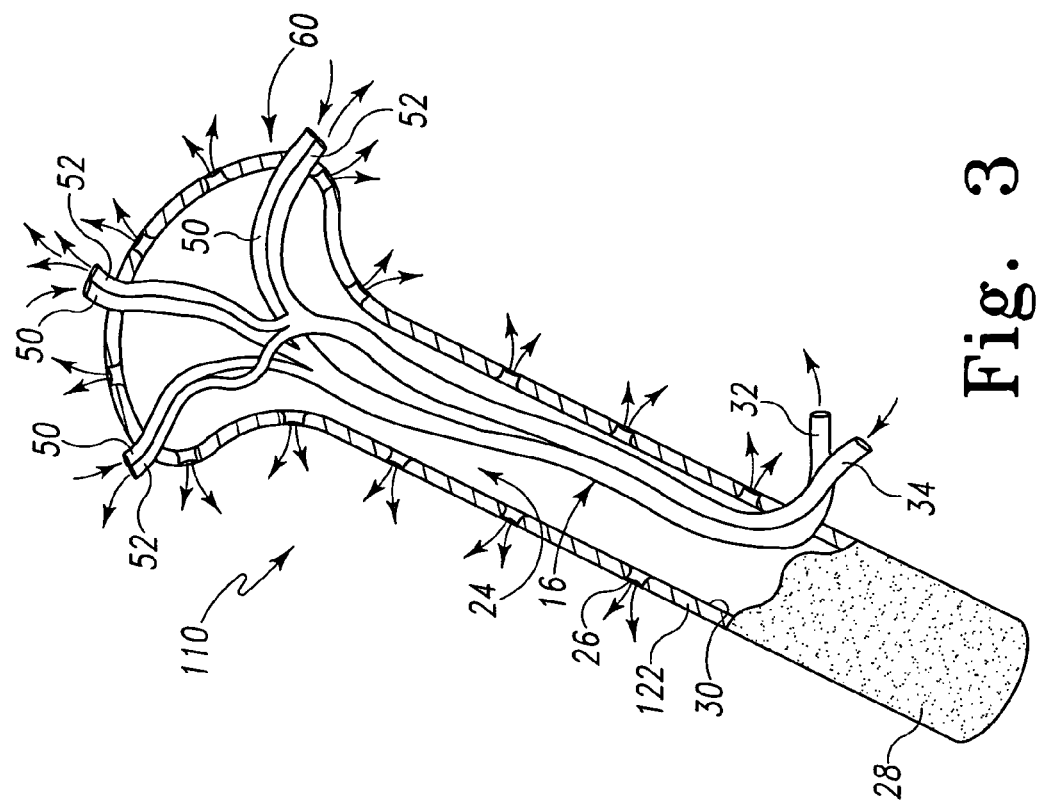
FIG. 3 is a sectional view of the orthopaedic implant shown in FIG. 2 showing the hollow support structure of the implant in an expanded position.
Figure 2:
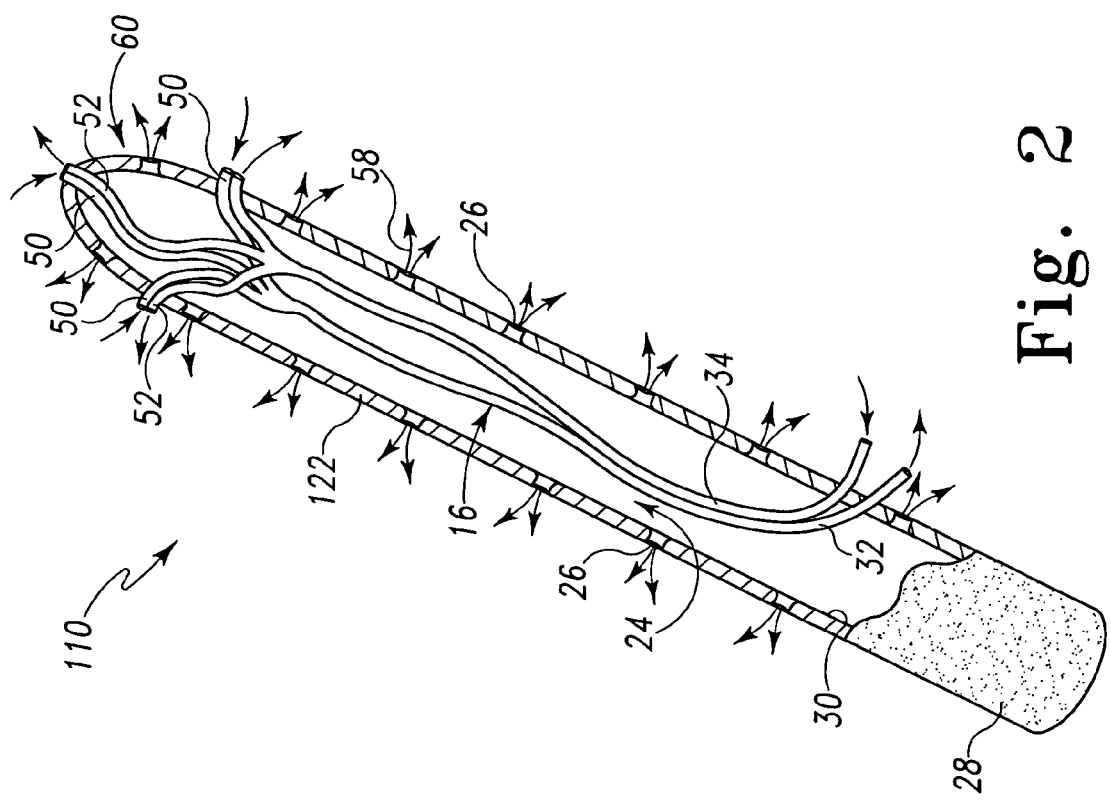
FIG. 2 is sectional view of another orthopaedic implant of the present disclosure for the treatment of AVN showing the implant including a hollow support structure in a retracted position and a synthetic vascular graft within the hollow support structure.

Looking now to FIGS. 2 and 3, another orthopaedic implant 110 for the treatment of AVN is provided. Similar to implant 10, implant 110 also includes a support structure or cannulated nail 114 and the synthetic vascular graft 16 shown in FIG. 1 and discussed above. Cannulated nail 114 is similar to cannulated nail 14 and the same reference numerals have been used to reflect like components. However, cannulated nail 114 includes an outer wall 122 having an open, proximal end (like that of outer wall 22) and a generally closed, distal end. The branches 50, 52 of the vascular graft 16 exit the distal end of the nail 114 through apertures 26 formed in the outer wall 122.

Implant 110 is expandable from a first, retracted position shown in FIG. 2 to a second, expanded position shown in FIG. 3. In the expanded position, a distal or head end 60 of the outer wall 122 is able to expand to fill a greater area of the necrotic portion 20 of the femoral head 12, for example. This expansion of the head end 60 into the necrotic area 20 provides further support to the femoral head 12 and particularly to the necrotic portion 20 of the femoral head 12. Further, the expanded head end 60 of the implant 110 provides a greater surface area of the implant 110 within the necrotic portion 20 of the femoral head 12 to be able to deliver bioactive and/or osteogenic agents to a greater area of the femoral head 12. For example, as mentioned above with respect to the implant 10 shown in FIG. 1, a device (not shown) may be used to inject osteogenic or other bioactive agents into the passageway 24 of the nails 14, 114. The fenestrated or porous nature of the nails 14, 114 then allows these agents to seep out through pores or openings 26 to affect the surrounding areas. The expandable head end 60 of nail 114 provides a greater surface area for presenting these agents to the surrounding areas. Further, the textured outer surface 28 of the expanded head end 60 may promote osteogenic activity in several dispersed nodes or areas of the head end 60 to further accelerate the establishment of new bone within the necrotic portion 20 of the femoral head 12.

As with the implant 10, the implant 110 is inserted into a predrilled passageway of the femoral head 12. The implant 114 is inserted, however, in its retracted position, shown in FIG. 2. Once fully inserted, the head end 60 of the implant 114 may then be expanded to consume a greater portion of the necrotic area 20 of the femoral head 12. Illustratively, the head end 60 of the implant 110 may be made of an expandable material such as an elastic balloon-type material which is expanded through the introduction of air or fluid pressure. Further, the head end 60 of the implant 110 may be expanded through the use of a tool (not shown) inserted into passageway 24 to engage the head end 60 and move the head end 60 from the retracted position to the expanded position. The tool may then be withdrawn from the nail 14.

Looking now to FIGS. 4 and 5, another implant 210 is provided having a cannulated nail 214 and the synthetic vascular graft 16 received within the cannulated nail 214, as discussed above and shown in FIGS. 1–3, for example. Similar to the cannulated nail shown in FIGS. 2 and 3, the cannulated nail 214 of FIGS. 4 and 5 includes an expandable head 260 which moves from a retracted position shown in FIG. 4 to an expanded position shown in FIG. 5. Similar to the expanding head end 60 of the implant 110 discussed above, the head 260 of the implant 210 of FIGS. 4 and 5 expands to provide additional structural support to the necrotic area 20 of the femoral head 12, to promote osteogenic activity in several dispersed nodes or areas of the head 260 to further accelerate the establishment of new bone, and also to allow any bioactive agents within the passageway 24 of nail 214 to seep out through the pores or openings 26 formed in the outer wall 22 of the nail 214 to affect the surrounding necrotic areas.

As best shown in FIG. 5, the head 260 of nail 214 includes three hollow prongs 262, 264, and 266. In the retracted position, each prong 262, 264, and 266 is adjacent to the outer surface 28 of a main body 268 of the cannulated nail 214. In the expanded position, however, each prong 262, 264, and 266 is spaced-apart from the outer surface 28. Each prong 262, 264, and 266 is hollow and includes an inner passageway 270 in communication with the main passageway 24 of the main body 268. Further an opening or aperture 272 is formed at a tip end of each prong 262, 264, and 266, as shown in FIG. 5. Illustratively, the synthetic vascular graft 16 is threaded through the main passageway 24 of the main body 268 of the cannulated nail 214 while the branches 50, 52 of the trifurcated end of the graft 16 are threaded through respective passageways 270 of each prong 262, 264, 266. For example, one pair of vascular branches including one venous branch 50 and one arterial branch 50 are threaded through one of the prongs 262, 264, 266 of the expandable head 260 of the nail 214.

Illustratively, the head 260 of the nail 214 may also include a port or opening 280 between the three prongs 262, 264, 266, as shown in FIG. 5, to allow one pair of vascular branches 50, 52 to be threaded therethrough for exiting the main passageway 24 of the implant 210 to transport blood to and from the necrotic area of the femoral head 12. Although the head 260 of the implant 210 is shown to include three prongs 262, 264, 266, it is understood that the head 260 may include any number of prongs which are movable between retracted and expanded positions. The prongs 262, 264, 266 may be spring-loaded to move to the expanded position once the head 260 of the implant 210 is positioned within the necrotic portion of the femoral head 12. An expanding device or tool (not shown) may be inserted within the main passageway 24 of the implant 210 may be used to engage the prongs 262, 264, 266 or an internal mechanism (not shown) attached to the prongs in order to move the prongs to the expanded position once the implant 210 is situated within the femoral head 12. It is also within the scope of this disclosure to remotely control the head 260 of the implant using radiofrequency energy, infrared energy, or a magnetic field, for example, to move the head 260 to the expanded position.

Figure 6:
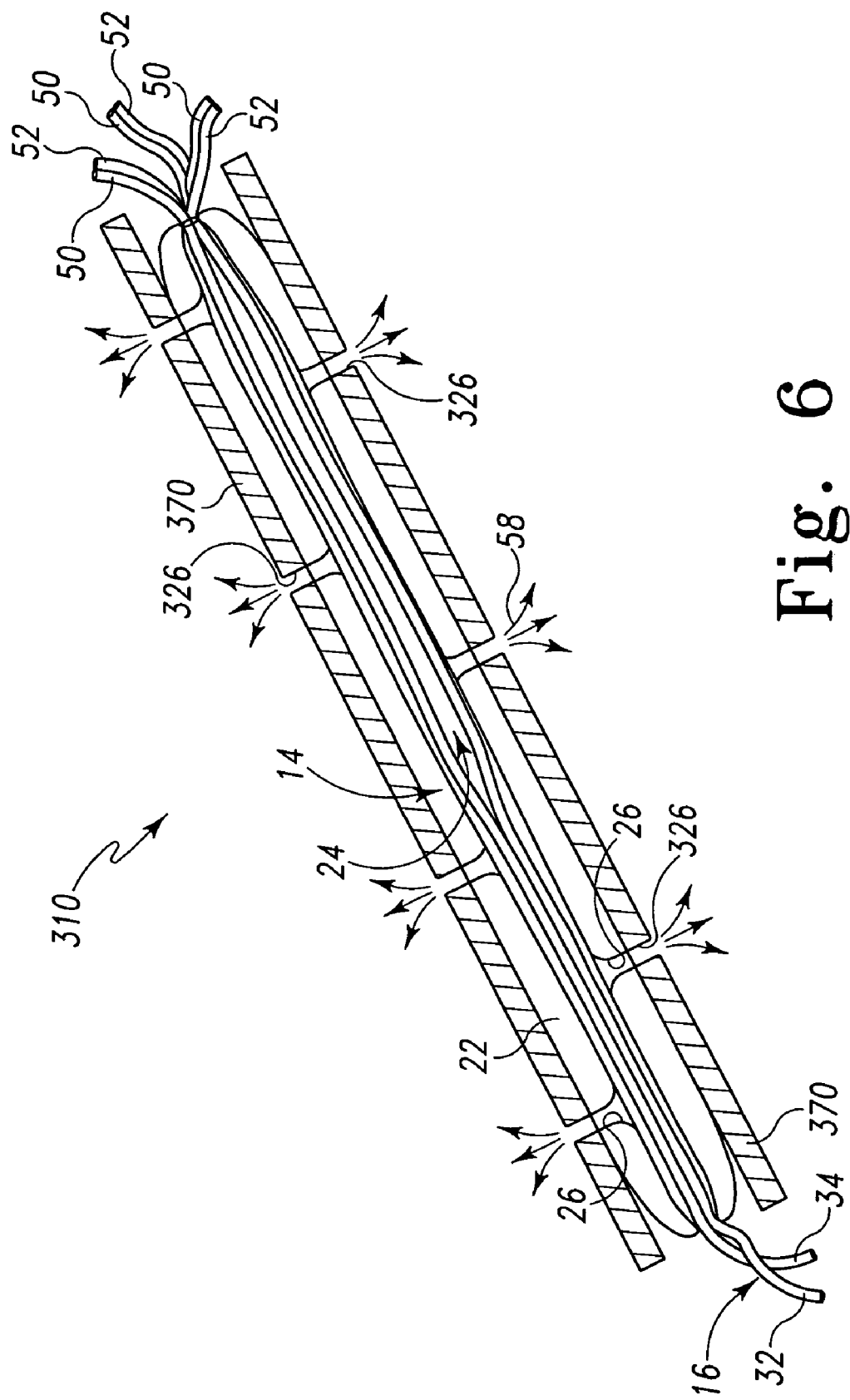
FIG. 6 is a sectional view of still another orthopaedic implant of the present disclosure for the treatment of AVN showing the implant including a hollow support structure, a synthetic vascular graft within the support structure, and an outer sheath surrounding the hollow support structure.

Looking now to FIG. 6, an orthopaedic implant 310 is provided which includes the cannulated nail 14 of FIG. 1 and the synthetic vascular graft 16 discussed above as well as an outer sheath 370. The outer sheath 370 surrounds the cannulated nail 14 to provide additional strength and stiffness to the implant 310. The outer sheath 370 may be made of a resorbable material such as a polymeric material, for example. Other suitable materials may be used as well. The outer sheath 370 may also include other bioactive agents which are slowly released and absorbed into the body. Illustratively, the outer sheath 370 is fenestrated to include openings or apertures 326 which correspond to the apertures 26 of the cannulated nail 14 to allow antibiotics, other drugs, or other bioactive agents introduced into the passageway 24 of the nail 14 to seep out through the nail 14 and through the opening or apertures 326 of the outer sheath 370 to the surrounding areas. The outer sheath 370 may also be porous and may include a textured outer surface to promote bone growth, etc. The outer sheath may also be mad of porous polymeric biomaterials imbibed with bioactive agents, drugs, antibiotics, etc. to enhance fixation, prevent infection, etc.

Looking now to FIGS. 7 and 8, an orthopaedic implant 410 is provided which includes a cannulated nail 414 and the synthetic vascular graft 16 discussed with respect to the other implants 10, 210, and 310. Similar to the implants 110 and 210, the cannulated nail 414 of the implant 410 is expandable from a retracted or collapsed position shown in FIG. 7 to an expanded position shown in FIG. 8. As discussed above, only the distal head end 60, 260 of the cannulated nails 114 and 214 of respective implants 110 and 210 moved from the retracted position to the expanded position. The cannulated nail 414 shown in FIGS. 7 and 8, on the other hand, includes a series of arms 480 positioned along a length of the cannulated nail 414 which moved from the retracted position shown in FIG. 7 to the expanded position shown in FIG. 8.

Illustratively, the cannulated nail 414 includes a main body 468 defining the inner passageway 24 which receives the vascular graft 16. Each arm 480 of the cannulated nail 414 is coupled to the main body 468 and movable relative to the main body 468 between the retracted and expanded positions. Further, each arm 480 is hollow and includes an inner passageway or branch 482 in communication with the main passageway 24. Similar to the arms 262, 264, 266 discussed above with respect to the implant 210 shown in FIGS. 2 and 3, each arm 480 of the implant 410 includes an opening 484 at a distal end of the arm 480 to provide an exit for bioactive agents, for example, introduced into the main passageway 24. Illustratively, as shown in FIGS. 7 and 8, the branches 50, 52 of the vascular graft 16 exit the inner passageway 24 of the main body 68 of the nail 4114 through a distal opening 490 of the main body 468. It is understood, however, that the branches 50, 52 or pairs of branches 50, 52 may also exit the nail 414 through one or more passageways 480 of the arms 480 and out the opening 484 at the end of each arm 480.

The arms 480 of the cannulated nail 414 may be spring-biased to the expanded position or may be manually moved to the expanded position by an expansion device or tool (not shown) which is inserted at least in part into the main passageway 24, for example, to either trigger a release-mechanism to allow the arms 480 to move to the expanded position or to directly move the arms 480 to the expanded position itself.

Figure 9:
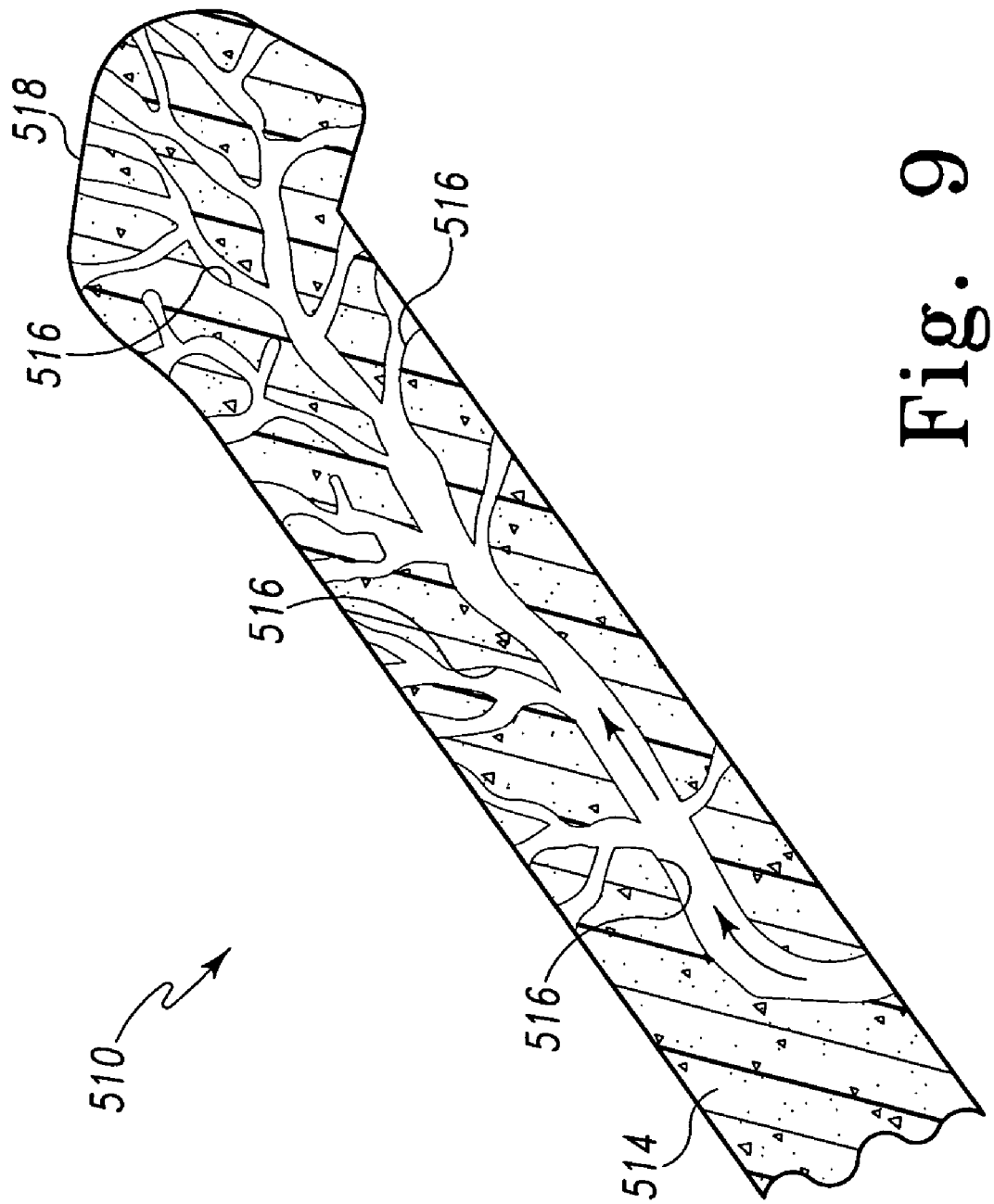
FIG. 9 is a sectional view of yet another orthopaedic implant of the present disclosure for the treatment of AVN showing a hollow, porous support structure of the implant formed to include a plurality of interconnected passageways which terminate at an outer surface of the support structure.

Looking now to FIG. 9, another orthopaedic implant 510 is provided which includes a porous nail 514 formed to include a plurality of passageways 516. Illustratively, the passageways 516 are interconnected and terminate at an outer surface 518 of the body of the nail 514. These passageways 516 are formed to provide a vasculature formation for fluid, such as blood, flow through the body of the nail 514. Further illustratively, the channels or passageways 516 may be coated with an extracellular matrix material, components of extracellular matrix material such as collagen, for example, elastin, fibronectin, etc., to promote attachment and differentiation of endothelial cells. The body of the nail 514 may provide cell attachment sites and surfaces for tissue regeneration and new endothelium formation to create vascular formation within the passageways 516. The nail 514 may be formed from suitable biological scaffold or material to be porous such as calcium phosphate, for example, as well as a metal sponge, a resorbable polymer, ceramic, and/or other materials discussed above with respect to implants 10, 110, 210, 310, and 410.

The implant 510 may be formed by mixing the material forming the biological scaffold, such as the calcium phosphate, for example, with an organic polymer such that the organic polymer occupies the areas where vasculature formation is desired. The organic polymer my then be dissolved and/or burned off to leave behind the channels or passageways 516 shown in FIG. 9.

It should be understood that although the orthopaedic implants 10, 110, 210, 310, 410, and 510 disclosed herein are shown to be used for the treatment of AVN and specifically for the treatment of AVN of the femoral head 12, the orthopaedic implants 10, 110, 210, 310, 410, and 510 maybe used for any large bone defect as well as other orthopaedic applications such as, for example, spinal fusion, nonunions, fracture repair, and trauma in general.

Figure 10:
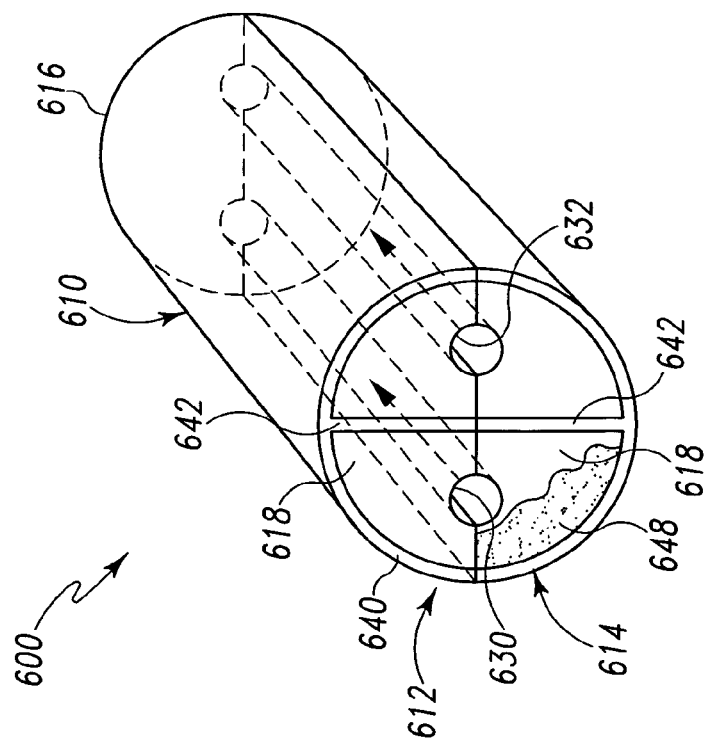
FIG. 10 is a perspective view of a plug for use with the implants disclosed herein to aide a surgeon or other technician in end to end attachment (or anastamosis) of the patient's native vein and artery structures to the synthetic vascular graft within the support structure of the various implants discussed above and showing the plug in a closed position and having first and second channels (shown in phantom) extending between a front and rear end of a body of the plug.
Figure 11:
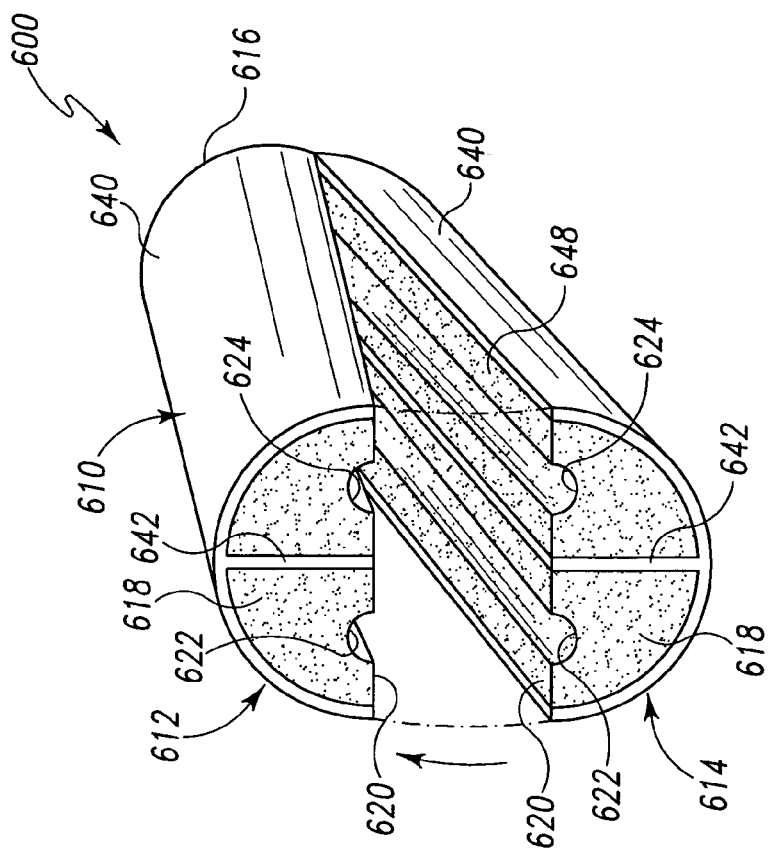
FIG. 11 is a perspective view of the plug of FIG. 10 showing the plug in an opened position.

Looking now to FIGS. 10 and 11, a plug 600 is provided to aide a surgeon or other technician in end to end attachment (or anastamosis) of the patient's native vein and artery structures, such as vein 40 and artery 42 shown in FIG. 1, for example, with the synthetic vascular graft 16 of implants 10, 110, 210, 310, and 410. Illustratively, the plug 600 includes a body 610 having an upper portion 612 and a lower portion 614. Each of the upper and lower portions 612, 614 have a generally semicircular cross-sectional shape. The upper and lower portions 612, 614 are hingedly coupled to each other near a first, rear end 616 such that the portions 612, 614 of the plug 600 are movable between a closed position, shown in FIG. 10, where front ends 618 of each of the portions 612, 614 are adjacent and engaged with each other and an opened position, shown in FIG. 11, wherein the front ends 618 of the portions 612, 614 are spaced-apart from each other.

Each of the upper and lower portions 612, 614 includes an inner, generally flat surface 620 having two generally parallel grooves 622, 624 formed therein which extend from the front end 618 to the rear end 616 of each portion 612, 614. When the plug 600 is in the closed position, therefore, the grooves 622, 624 formed in the upper portion 612 align with the corresponding grooves 622, 624 formed in the lower portion 614 to form two passageways 630, 632 through the body 610 of the plug 600. As is discussed in greater detail below, the passageway 630 is provided to receive the venous component 32 of the synthetic vascular graft 16 and the corresponding vein 40 of the patient. Further, the passageway 632 is provided to receive the arterial component 34 of the synthetic vascular graft 16 and the corresponding artery 42 of the patient.

Illustratively, the body 610 of the plug 600 includes a dense bioceramic outer shell 640. Further, each of the upper and lower portions 612, 614 include a dense bioceramic barrier or partition 642 running lengthwise from the front end 618 to the rear end 620 of the body 610 to create two separate chambers of each portion 612, 614. Each chamber is filled with a porous ceramic filler and the illustrative grooves 622, 624 are formed through the porous ceramic filler 648. The pores of the ceramic filler 648 may be coated with a blood clotting agent.

The plug 600 may be coupled to the support structure of the implant by a bioresorbable polymer layer of material (not shown) which may also act as the hinge between the upper and lower portions 612, 614 of the plug 600. The ends of the synthetic venous component 32 and arterial component 34 of the implant terminate within and are attached to the rear end 620 of the corresponding grooves 622, 624 of one of the portions 612, 614 of the plug 600.

A reinforcing tube (not shown) formed of an absorbable material such as electrospun collagen, for example, may be inserted into each of the venous and arterial components 32, 34 of the synthetic vascular graft 16. The patient's native vein 40 and artery 42 are then located, isolated, and prepared by the surgeon or other technician and are placed at or near the front end 618 of the plug 600 within the grooves 622, 624 of the same portion 612, 614 to which the synthetic grafts 32, 34 are coupled and are slid over the corresponding electrospun collagen reinforcement tubes (not shown) coupled to the synthetic vascular grafts 32, 34. A fibrin based glue may be used to seal around the abutted ends of the native and synthetic arterial and venous tubes. Illustratively, the clotting agent contained in the porous ceramic filler operates to seal off flow from any minor leaks which may develop.

Once the surgeon is satisfied that no leaks have developed, the plug 600 is moved to the closed position to enclose the abutted ends of the synthetic and native arterial and venous structures within the passageways 630, 632. The plug 600 may then be inserted into the cavity 62 predrilled through the femur. The body 610 of the plug 600 may have a diameter which is slightly larger than a diameter of the cavity 62 drilled in the femur such that the plug 600 may be press-fit into the cavity 62 to hold the upper and lower portions 612, 614 of the body 610 tightly together in the closed position and to aid in anchoring the plug 600 in place within the femur.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. An orthopaedic implant for the treatment of avascular necrosis of the bone, the orthopaedic implant comprising:
   a hollow support structure defining a passageway and having a proximal opening and a distal opening, and a synthetic vascular graft received, at least in part, within the passageway of the hollow support structure such that a proximal end portion of the synthetic vascular graft is received through the proximal opening of the hollow support structure and a distal end portion of the synthetic vascular graft is received through the distal opening of the hollow support structure, wherein the vascular graft includes a venous tube and an arterial tube fluidly isolated from the venous tube.

2. The orthopaedic implant of claim 1, wherein the hollow support structure includes a plurality of fenestrations between the proximal opening and the distal opening configured to provide communication between the passageway of the hollow support structure and the surrounding environment.

3. The orthopaedic implant of claim 1, wherein the hollow support structure includes a textured outer surface.

4. The orthopaedic implant of claim 3, wherein the hollow support structure includes a textured inner surface.

5. The orthopaedic implant of claim 3, wherein the textured outer surface has approximately a 60 nanometer surface roughness.

6. The orthopaedic implant of claim 1, wherein the hollow support structure includes one or more of the following: a metal sponge; a resorbable polymer; and ceramic.

7. The orthopaedic implant of claim 1, wherein a distal end of the venous tube is triftircated and a distal end of the arterial tube is trifurcated.

8. The orthopaedic implant of claim 1, wherein the venous tube and the arterial tube each have a diameter of approximately 3–6 mm and a length of approximately 15 cm.

9. The orthopaedic implant of claim 1, wherein the vascular graft includes a protein-based polymer.

10. The orthopaedic implant of claim 9, wherein the protein-based polymer includes one or more of the following: self-assembled collagen, self-assembled extracellular basement membrane extracts; electro-spun collagen; elastin; and silk.

11. The orthopaedic implant of claim 1, wherein the hollow support structure includes a main body defining the passageway and an arm coupled to the main body and movable between a collapsed position adjacent to and engaged with the main body and an expanded position spaced-apart from the main body.

12. The orthopaedic implant of claim 11, wherein the arm includes a channel in fluid communication with the passageway of the main body.

13. The orthopaedic implant of claim 11, wherein the hollow support structure includes a plurality of arms movable between retracted and expanded positions.

14. The orthopaedic implant of claim 13, wherein the arms are positioned at a distal end of the main body.

15. The orthopaedic implant of claim 13, wherein the arms are positioned along a length of the main body.

16. The orthopaedic implant of claim 1, further including a resorbable outer sheath surrounding the hollow support structure.

17. A method of vascularizing a necrotic portion of a bone comprises the steps of:

inserting a synthetic vascular graft into a passageway of a hollow support structure, implanting the hollow support structure and the synthetic vascular graft into a predrilled channel of the bone, and suturing the synthetic vascular graft to a vein and artery of the bone.

\* \* \* \* \*